(12) United States Patent
Alex et al.

(10) Patent No.: US 9,084,769 B2
(45) Date of Patent: Jul. 21, 2015

(54) COMPOSITIONS COMPRISING NON STEROIDAL ANTI-INFLAMMATORY DRUGS AND METHODS FOR USE THEREOF

(71) Applicants: Phillip Alex, Abingdon, MD (US); Ben Johns, Scotch Plains, NJ (US)

(72) Inventors: Phillip Alex, Abingdon, MD (US); Ben Johns, Scotch Plains, NJ (US)

(*) Notice: Subject to any disclaimer, the term of this patent is extended or adjusted under 35 U.S.C. 154(b) by 0 days.

(21) Appl. No.: 13/705,552

(22) Filed: Dec. 5, 2012

(65) Prior Publication Data
US 2013/0142869 A1 Jun. 6, 2013

Related U.S. Application Data

(60) Provisional application No. 61/566,765, filed on Dec. 5, 2011.

(51) Int. Cl.
| | | |
|---|---|---|
| *A61K 31/7016* | (2006.01) |
| *A61K 33/30* | (2006.01) |
| *A61K 31/167* | (2006.01) |
| *A61K 31/192* | (2006.01) |
| *A61K 31/415* | (2006.01) |

(52) U.S. Cl.
CPC .............. *A61K 33/30* (2013.01); *A61K 31/167* (2013.01); *A61K 31/192* (2013.01); *A61K 31/415* (2013.01); *A61K 31/7016* (2013.01)

(58) Field of Classification Search
CPC . A61K 2300/00; A61K 31/7016; A61K 33/30
USPC .................................. 424/641, 451, 474, 490
See application file for complete search history.

(56) References Cited

U.S. PATENT DOCUMENTS

2010/0150861 A1* 6/2010 Geibel et al. ................. 424/85.2

OTHER PUBLICATIONS

Watanabe et al. Prebiotic Properties of Epilactose. Aug. 5, 2008. J. Dairy Sci. pp. 4518-4526.*
Lanza et al. NSAID-induced gastric ulceration is dose related by weight: an endoscopic study with flurbiprofen. May 1993. Am J Gastroenterol. Abstract.*

* cited by examiner

*Primary Examiner* — Frederick Krass
*Assistant Examiner* — Tracy Liu
(74) *Attorney, Agent, or Firm* — Christina Chamberlin

(57) ABSTRACT

The invention provides analgesic, antipyretic and anti-inflammatory compositions containing epilactose in combination with non-steroidal anti-inflammatory drugs and pharmaceutically acceptable zinc compounds. This invention relates to the use of these novel compositions for significantly improved and synergistic safety and therapeutic profiles.

14 Claims, 5 Drawing Sheets

COMPOSITIONS COMPRISING NON STEROIDAL ANTI-INFLAMMATORY DRUGS AND METHODS FOR USE THEREOF

FIELD OF THE INVENTION

The present invention relates to the combination of pharmaceutical compositions comprising of epilactose, a non-steroidal anti-inflammatory drug, and an appropriate zinc compound, and the use thereof for the safe, effective, and pronounced treatment of pain, inflammation and fever. The present invention is also directed to methods of preparation of disclosed pharmaceutical compositions with all key ingredients in different embodiments in pharmaceutically effective amounts that maintain synergy in their efficacy for the intended clinical use.

BACKGROUND OF THE INVENTION

Non-steroidal anti-inflammatory drugs (NSAIDs) form a very large category of drugs that are primarily used to reduce fever, pain and inflammation. As the name implies, they do not act via the same path as steroids that suppress the immune system from producing fever and pain. NSAIDs are also non-narcotic and their sub-categories are based on their chemical structure. They differ in not only form, but also which enzymes they inhibit and for how long.

Among the 'Salicylates' sub-category, the most famous drug is aspirin known to be an effective pain killer. It also has other therapeutic uses such as effective blood thinner. Other known drugs in this sub-category are salicylamide, salicyl salicylate, methyl salicylate, magnesium salicylate, faislamine, ethenzamide, diflunisal, choline magnesium salicylate, benorylate/benorilatem and amoxiprin.

Another sub-category is constituted by 'Arylalkanoic acids', which has an aryl group on one of the rings of the drug molecule. The drugs in this sub-category presently in use are aceclofenac, acemetacin, alclofenac, bromfenac, diclofenac, etodolac, indometacin, nabumetone, oxametacin, proglumetacin, sulindac, and tolmetin.

The '2-Arylpropionic acids' are an important sub-category and tends to have an ending of 'profen' in their generic names. The known drugs in this sub-category are alminoprofen, benoxaprofen carprofen, dexibuprofen, dexketoprofen, fenbufen, fenoprofen, flunoxaprofen, flurbiprofen, ibuprofen, ibuproxam, indoprofen, ketoprofen, ketorolac, loxoprofen, naproxen, oxaprozin, pirprofen, suprofen, tiaprofenic acid.

Another sub-category of NSAIDs is collectively known as 'N-Arylanthranilic acids'; the generic drugs in this sub-category tend to have ending of 'fenamic acids' and the well known drugs are mefenamic acid, flufenamic acid, meclofenamic acid, and tolfenamic acid.

'Oxicams' is yet another sub-category of NSAID, which are essentially enolic acid (e.g., a double bond between two adjacent carbon atoms and a hydroxyl containing molecules) that exhibit keto-enol tautomerism. The well known drugs in this sub-category are droxicam, lomoxicam, meloxicam, piroxicam, and tenoxicam.

Another sub-category is characterized as 'Pyrazolidine' derivates; pyrazolidine is a five member ring with two nitrogen atoms adjacent to each other that bear different functional groups. The well known drugs in this sub-category are ampyrone, azapropazone, clofezone, kebuzone, metamizole, mofebutazone, oxyphenbutazone, phenazone, phenylbutazone, sulfinpyrazone.

Finally, another important sub-category of NSAIDs is known as 'COX-2 Inhibitor' for their ability to inhibit COX-2 enzyme selectively which was considered clinically very significant. Selective NSAIDs (also called COX-2 inhibitors) are as effective in relieving pain and inflammation as nonselective NSAIDs but are less likely to cause gastrointestinal injury. Due to their decreased potential to cause ulcers or gastrointestinal bleeding, selective NSAIDS such as celecoxib are sometimes recommended for people who have had a peptic ulcer, gastrointestinal bleeding, or gastrointestinal upset when taking other nonselective NSAIDs. However, many of the drugs in this sub-category have been withdrawn from the US market in view of other observed side effects, which include valdecoxib, rofecoxib, parecoxib, etoricoxib. Lumiracoxib is known to have been put on watch list; the only drug in this sub-category available commercially is celecoxib. Numeslide, also a COX-2 inhibitor has been withdrawn in many countries due to adverse effects.

NSAIDs have strong anti-inflammatory, antipyretic, and analgesic properties, and are used for the treatment of a variety of acute and chronic conditions associated with pain, fever and inflammation. Some of the conditions that NSAIDs are widely used include rheumatoid arthritis, osteoarthritis, ankylosing spondylitis, inflammatory arthropathies, acute gout, dysmenorrhoea, metastatic bone pain, headache and migraine, postoperative pain, pyrexia, ileus, renal colic, and in pain associated with injuries and dental procedures. The principal pharmacological effects of NSAIDs in reducing the pain and inflammation have been demonstrated to be due to their potential to inhibit enzymes, called cyclooxygenase, which in turn inhibit prostaglandin synthesis. Cyclooxygenase enzyme inhibition is also responsible for many of the side effects of NSAIDs. Two main types of NSAIDs are known as 'selective' and 'nonselective' depending on their ability to inhibit specific types of cyclooxygenase (COX) enzymes. Nonselective NSAIDs are known to inhibit both COX-1 and COX-2 enzymes whereas selective NSAIDs preferentially inhibit COX-2 enzymes found at the sites of inflammation more than the COX-1 enzymes normally found in the stomach, blood platelets and blood vessels.

Most nonselective NSAIDs, such as aspirin, ibuprofen, naproxen etc. are commonly available without prescription in most countries and belong to 'Over-the-counter (OTC)' group. Most people also tolerate NSAIDs without any problem when taken occasionally. However, side effects occur and are frequently encountered when the drugs are necessarily taken on long-term basis.

The clinical utility of NSAIDs is significantly limited due largely to their ability to cause a diverse array of toxicities, particularly of those in the gastrointestinal tract, renal, and cardiovascular systems. The most common side effects and associated risks of their use due to their toxicities include the following:

Gastrointestinal system: While short term use of NSAIDs can cause stomach upset (dyspepsia), their long term use, especially at high doses, can lead to peptic ulcer and bleeding of the upper gastrointestinal tract in the stomach. These side effects are caused by NSAIDs inhibiting the COX-1 enzyme resulting into decrease of mucous production in cells lining of the gastrointestinal tract, leaving it vulnerable to gastric acid, bile, enzymes, and alcohol. Gastrointestinal injuries range from heartburn, nausea, erosion and abdominal pain to serious complications such as ulcers and hemorrhage (Shoenfeld P, M O Kimmey, J. Scheiman, D. Bjorkman, L. Laine, *Aliment Pharmacol Ther* 1999; 13:1273-1285). COX-1 has been found to be responsible for protecting the stomach through mucous membrane and immune cell defense, maintaining blood flow and kidney function, and processing sensations.

Kidney Toxicity: A comprehensive review of nephro-toxicity of existing NSAIDs suggested that the adverse effects of NSAIDs are mediated via inhibition of prostaglandin synthesis from arachidonic acid by non-specific blocking of the enzyme cyclooxygenase leading to vasoconstriction and reversible mild renal impairment in volume contracted states. (Ejaz P, Bhojani K, Joshi V R; *J. Assoc. Phys. India*, Vol 52, 2004, pp 632-640) This could lead to acute tubular necrosis and acute renal failure when unopposed. In patients on long term NSAIDs without acute or chronic renal failure, subclinical renal dysfunction such as reduced creatinine clearance and impaired urine concentrating ability has been observed. This sub-clinical dysfunction, although reversible on withdrawal of NSAIDs in most cases, some cases of persistent residual dysfunction have also bean reported. The authors conclude that despite a wide range of NSAIDs being available, a renal safe NSAID is yet to be discovered.

It has been determined that use of COX-2 inhibitors increases the chances of having a heart attack. Further, most NSAIDs, including COX-2 inhibitors boost blood pressure and could counteract the effect of some blood-pressure drugs. They have also been shown to impair blood vessels' ability to relax and may stimulate the growth of smooth muscle cells inside arteries leading to clogging of arteries, a process known as atherosclerosis.

Other Toxicities: One of the other toxicities associated with the use of NSAIDs is the 'Liver toxicity'; the long term use of NSAIDs, especially at high doses, is reported to harm the liver. Ringing in the ears (tinnitus) is another malady reported by many people on high doses of aspirin or other NSAIDs. Further, anyone who has a cardiovascular disease (i.e., coronary artery disease or angina) may have a further increase in risk of heart attacks when taking an NSAID other than aspirin which is sometimes recommended in low doses to people with coronary artery disease to reduce the risks of developing a blood clot.

Regimens of NSAID therapy, therefore, include administration of antacids (acid neutralization), and cimetidine, ranitidine and famotidine (acid secretion inhibition) as a matter of necessity as of now and the search for a better and safe composition of NSAID remains a challenge particularly where the therapy must be protracted for a long time, e.g., in treatment of rheumatoid arthritis in old people.

Novelty Search

The present invention is targeted to address the problems associated with toxicities, particularly the gastrointestinal, cardiovascular, and renal toxicities described above. The novelty search presented below would show that effective compositions based on the 'triple combination' as disclosed in this application which precisely ameliorate the side effects associated with renal and gastrointestinal toxicities of NSAIDs have not been discovered or reported before.

Many different researchers have therefore attempted different strategies to find acceptable solutions. Some researchers designed cyclo-oxygenase-2 (COX-2) inhibitors which were claimed to be devoid of ulcer-promoting effects but this premise remained unfulfilled clue to concerns about the cardiovascular safety of COX-2 inhibitors. Others used a group of drugs commonly known as 'proton-pump inhibitors' as part of NSAID composition essentially to reduce gastric acid production during NSAID administration. Another group of drugs known as 'H2-receptor' producing similar effects however working through a different mode of action have also been incorporated in NSAID compositions. Then there have also been attempts to formulate the compositions in the nano particles range to enhance the dispersion of active ingredient and incorporation of substances that would enhance the bioavailability of the compositions.

U.S. Pat. No. 4,873,231 disclosed a possible mode of decreasing the toxicity of a salt of ibuprofen by combining with suitable amounts of bicarbonate or carbonate.

U.S. Pat. No. 5,155,118 uses substituted imidazoles for preventing NSAID-induced renal failure by administering these separately or as NSAID composition.

U.S. Pat. No. 5,213,807 utilized curative property of prostaglandin in NSAIDs formulation through a three layered coaling having commercially available prostaglandin, misoprostol in the mantle core. Similarly, U.S. Pat. No. 6,656,503 (EP1068867), U.S. Pat. No. 7,303,761 and also U.S. Pat. No. 6,740,340 (WO99/65496) disclose similar use of prostaglandins in NSAIDs formulations.

U.S. Pat. No. 6,926,907 (EP2163241A1) provides dosage forms capable of releasing an agent that raises the pH of a patient's gastrointestinal tract prior to the release of non-steroidal anti-inflammatory drug.

U.S. Pat. No. 4,757,060 and U.S. Pat. No. 5,037,815 disclose NSAID compositions having an H1 receptor blocker such as diphenhydramine and/or its salt, ethanolamines, ethylenediamines, alkylamines and piperazines and/or their salts and an H2 receptor blocker such as cimetidine, ranitidine, famotidine and/or their salts to reduce gastrointestinal injury.

U.S. Pat. No. 7,488,497, U.S. Pat. No. 6,365,184, U.S. Pat. No. 6,613,354 and US2002155153 employ proton pump inhibitors, lansoprazole, pantoprozole and S-omeprazole and/or their salts in NSAID compositions for reduction of gastric acid for better patient compliance which are otherwise used most often separately while administering NSAID.

WO2011/144994A1 uses esomeprazole magnesium dihydrate as acid blocker where as US2009233970A1 uses ranitidine as acid blocking agent with NSAIDs such as ibuprofen and naproxene.

U.S. Pat. No. 4,766,117 provides an improved anti-inflammatory composition of piroxicam or its salt with analgesic acetaminophen, antidepressant doxepin, bronchodilator pirbuterol, minor tranquilizer diazepam, or antihypertensive trimazosin wherein acetaminophen has been selected for its reported property of reducing the ulcerogenicity of aspirin and doxepin has been used for its reported gastric antisecretory activity.

U.S. Pat. No. 5,185,144 discloses oral compositions containing a gastroprotective amount of zirconium-aluminum glycinate (ZAG), aluminum chlorohydrate (ACH) or a mixture thereof for protecting the gastric mucosa against injury caused by a gastric irritant.

U.S. Pat. No. 5,811,410 utilizes administration of therapeutically effective dose of hyaluronic acid or a non-toxic salt thereof immediately following or at the same time as the treatment with the NSAID wherein it is postulated that hyaluronic acid facilitates the transport of the agent to the site through membranes of the individual cells to be treated and also effectively counteracts the toxic side effects such as gastro-intestinal distress, neurological abnormalities, depression, etc. U.S. Pat. No. 5,847,002 and U.S. Pat. No. 6,159,955 (WO97/03699) provide other variants of NSAID compositions involving hyaluronic acid.

WO2007086931 uses synergistically effective amounts of vitamins C & E and DHA with a preferred NSAID for prevention of the onset and/or progression of dementia or Alzheimer's disease in individuals at increased risk thereof. Likewise WO2010069493A1 uses quinolone antibiotic with NSAID for veterinary use. And WO2010069493A1 uses quinolone antibiotic with NSAID for veterinary use.

US2007093457 uses curcumin with an NSAID to effectively reduce the dose of NSAID in the treatment of cancer and inflammation.

U.S. Pat. No. 5,183,829, U.S. Pat. No. 5,518,736 and U.S. Pat. No. 5,552,160 using nano-technological concepts employ surface modifiers adsorbed on crystalline NSAID maintaining an effective average particle size of less than about 400-1000 nm which are reported to act as dispersing agents for the active ingredients; these formulations exhibit reduced gastric irritation and hasten onset of action. US2007134339A1 uses zonisomide, an antiseizure drug as a component with a preferred NSAID at nanoscale of 2000 nm for a formulation stated to be effective for migraine. Likewise US2009311335 with its family of patents, viz., EP2320893, WO2009152192, JP2011524358 and CA2723998 use triptan, a drug for migraine in combination with NSAID for treatment of migraine wherein the triptan is in a controlled release matrix and the NSAID is essentially in the nanoparticulate range of 2000 nm for its enhanced bioavailability.

Many biotechnological approaches have also been adopted to modify the compositions and/or preventing side effects of NSAIDs administration. WO/1998/046249A1 provides methods and compositions for administration of a pharmaceutically effective amount of vascular endothelial cell growth factor (VEGF), produced in several isoforms through r-DNA technology to treat various forms of ulcers including those induced from NSAIDs and other drugs.

U.S. Pat. No. 5,772,999 teaches a method of preventing, countering, or reducing NSAID-induced gastrointestinal damage by administering milk or egg products from animals hyper-immunized with an antigenic or genetic vaccine to the subject undergoing treatment with NSAID administration.

Analogs of somatostatin, a peptide hormone [also known as growth hormone-inhibiting hormone (GHIH) or somatotropin release-inhibiting factor (SRIF)] that regulates the endocrine system and has been shown to have potent inhibitory effects on various secretory processes in tissues such as pituitary, pancreas and gastrointestinal tract have been utilized in the NSAIDs compositions reported in EP0671413.

U.S. Pat. No. 6,017,932 have reportedly achieved enhanced bio-availability of NSAIDs composition containing piperine, its metabolites, structural analogues or isomers which are already extensively used in Indian system of medicine for similar purposes in other Indian ayurvedic drugs.

Despite scores of inventions reported in patent and non-patent literature as described above, there still is a need for simple and effective NSAID compositions and the treatment based on the same that can alleviate and prevent NSAID-induced gastrointestinal damage and chronic gastrointestinal disorders as well as renal failure, without the complication of side effects. The inventors and the applicant herein, therefore, undertook this development task and adopted a radically different and novel approach to produce NSAID compositions of highly improved characteristics and minimal side effects unreported hitherto.

The prime objects of this invention will be realized by those skilled in the art from the following disclosure which refers to key ingredients of the compositions and their utility in the formulations and their clinical results.

BRIEF SUMMARY OF THE INVENTION

The primary object of this invention was to develop highly safe and effective compositions of non-steroidal anti-inflammatory drugs, the clinical use of which continues to grow globally often on long term basis in high doses despite well known side effects and health related risks. Of the various side effects that NSAIDs produce, the gastrointestinal as well as renal failure constitutes a major problem.

Accordingly, in one aspect of the present invention, there is provided a triple combination of a preferred NSAID, epilactose and a zinc salt, a composition based on which and comprising of effective amounts of each component provide a highly potent drug for certain indications with no or unexpectedly minimal side effects and toxicities elaborated above.

In other embodiments, a composition based on the combination of a preferred NSAID and epilactose, without the third component of any zinc salt as before useful for treatment of certain other indications may be as effective and devoid of observable side effects. Both epilactose and the chosen zinc salt indicate interaction with functional groups of the active ingredient of the chosen NSAID and the metabolic processes during the treatment of mammals for certain indications.

Thus, epilactose together with or without a suitable zinc salt were conceived to be ideal constituents) in the new formulations enhancing the bioavailability of the drug and improving its absorption characteristics in the intestine, further enabling the inventors to hypothesize and demonstrate that NSAIDs compositions together with these constituents produce a considerable, more than additive, synergistic effect.

Novel and highly synergistic triple pharmaceutical compositions of NSAIDs with epilactose and zinc have thus been disclosed in this invention. Triple and double pharmaceutical compositions of selected NSAIDs with different amounts of epilactose together with a suitable zinc salt or using them individually were prepared in the laboratory using standard preparatory methods in the preferred embodiments to test the hypothesis of synergistic efficacy. Several experimental conditions were tested with these compositions against single component doses of key NSAID used in the above formulations as well as other single component NSAIDs and plain epilactose and a relevant zinc salt far comparison purposes. In this way, test compositions as obtained were designated as Ibu+Epi+ZnCar, Ibu+Epi+ZnCl, Ibu+ZnCar, Ibu+ZnSt, Ibu+ZnCl, Ibu+Epi where 'Ibu' refers to ibuprofen as the selected NSAID, 'Epi' refers to epilactose which is one of the essential key component of this invention, 'ZnCar' refers to zinc carnosine, a selected zinc salt in the preferred embodiment, 'ZnCl' refers to zinc chloride as another selected zinc salt in the preferred embodiment, 'ZnSt' refers to zinc stearate as another selected zinc salt in the preferred embodiment.

These compositions were used for pre-clinical tests on animal models to test for their efficacy against a range of studies using single components of epilactose (Epi), zinc salt (Zn) or zinc carnosine (ZnCar), along with single components of selected NSAIDs, viz., ibuprofen (Ibu), naproxen (Nap) and celecoxib (Cox). Standard GLP protocols were used in carrying out pre-clinical studies and efficacy tests against pain, inflammation, ulcerogenicity, and hemoglobin loss. To further evaluate the role of synergistic interactions between the different combinations, an isobolographic analysis was conducted on the safety index from the gastrointestinal, hemoglobin and renal studies conducted herein on all NSAID formulations. The experimental results not only demonstrate the gastroprotective, vascular, and renoprotective safety profiles of these compositions but a remarkable synergistic property of the triple combination which forms a key discovery of this invention. Histopathological investigations carried on these preclinical studies showed dramatic resolution of signs with these new improved triple compositions.

All publications from patented or non-patented literature mentioned in this specification under 'Novelty Search' or elsewhere are herein incorporated by reference and for the purpose of providing a context for the present invention. It is not to be taken as an admission that any or all of the concepts and related results of experimental findings as disclosed herein together with those references form part of the prior art base or were common general knowledge in the field relevant to the present invention as if existed anywhere before the priority date of this application. The features and advantages of composition(s) of the present invention will become further apparent from the following detailed description of preferred embodiments.

DETAILED DESCRIPTION OF THE INVENTION

Figure 1:
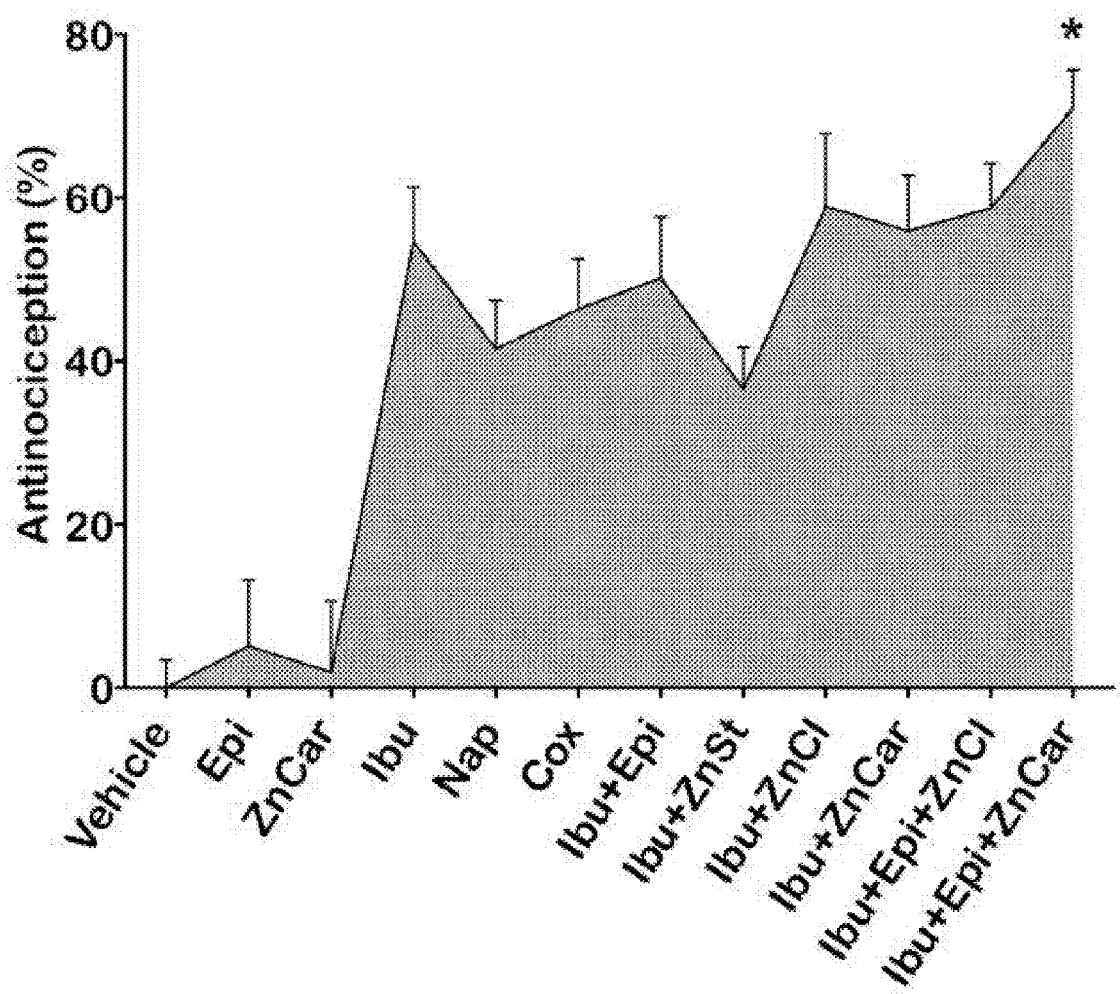
FIG. 1 is a graph demonstrating the efficacy of NSAID+ Epi+Zn with relevance to the treatment of pain.

The key discovery of this invention is a triple combination of a NSAID of a choice with epilactose and a zinc salt for the treatment of pain, inflammation, and fever. The results of pre-clinical trials of these triple combinations were found to be synergistically superior in excess of combinations of NSAIDs either with epilactose, or that of NSAID with an appropriate zinc salt. The synergistic effect of the triple combination of NSAID, epilactose and zinc salt is of great clinical and practical utility; therefore, this triple combination forms a primary claim of this invention.

The inventive features of this invention are based on the choice of key constituents, i.e., epilactose and an appropriate zinc salt. Following a broad-based screen of signaling mechanisms and biomarkers after an in-vitro based induction treatment with NSAIDs, it was hypothesized by the inventors that epilactose in combination with that of an appropriate zinc salt would improve the pharmacokinetics of NSAID drugs by way of promoting bioavailability and absorption of the drug in the intestine.

Epilactose (4-O-β-galactopyranosyl-d-mannose) is a rare nondigestible disaccharide with very limited information on its biological and pharmacological effects. Epilactose was demonstrated to promote intestinal calcium and iron absorption from the small intestine of rats and was also shown to proliferate human bifidobacteria thereby demonstrating its potential for use as a probiotic. (*Ingestion of Epilactose, a Non-digestible Disaccharide, Improves Postgastrectomy Osteopenia and Anemia in Rats through the Promotion of Intestinal Calcium and Iron Absorption*, Suzuki Takuya, Megumi Nishimukai, Aki Shinoki, Hidenori Taguchi, Satoru Fukiya, Atsushi Yokote, Wataru Saburi, Takeshi Yamamoto, Hiroshi Hara, and Hirokazu Matsui; *J. Agric. Food Chem.*, 58 (19), pp 10787-10792 (2010). (*Effects of epilactose on calcium absorption and serum lipid metabolism in rats*, Nishimukai M, Watanabe J, Taguchi H, Senoura T, Hamada S, Matsui H, Yamamoto T, Wasaki J, Hara H, Ito S.; *J Agric Food Chem.* (2008);56(21):10340-5.)

Zinc has been documented to have cyto protective effects in the gastro intestinal tract, facilitate healing of ulcers, attenuate helicopylori induced gastritis in mice, and ameliorate indomethacin-induced oxidative stress. However, zinc has also been shown to interact with NSAIDs and could reduce the absorption and effectiveness of these medications. Nonetheless, pharmaceutically acceptable water soluble zinc salts have been employed successfully in several pharmaceutical compositions to enhanced bioavailability of therapeutic agents e.g., on WO/2009/017624. Enhanced bioavailability via zinc complexes of NSAIDs (e.g., indomethacin and naproxene) are also available in the scientific literature in public domain (i. *Bioavailability of indomethacin from zinc-indomethacin complex*, Singla, A K, D K Mediratta, and Kamla Pathak, *Int J Pharma*, vol. 60, 27-33 (1990); ii. *Zinc-indomethacin complex: synthesis, physiochemical and biological evaluation in the rat*, Singla, A K and Hardeep Wadhwa, *Int J Pharma*, vol 120, 145-155 (1995) iii. *Zinc-naproxene complex: synthesis, biological evaluation*; Sharma, Jyoti, A K Singla, and S Dhawan, *Int. J Pharma*, vol 260, 217-227 (2003)

The conception of the present invention was reduced to practice by the present inventors by identifying and developing novel compositions containing a triple combination of a NSAID of choice, epilaetose, and zinc, duly abbreviated as NSAID+Epi+Zn in this application and successfully demonstrating the triple composition to have novel synergistic effects and significant safety therapeutic profiles when compared to single or individual formulations of NSAID, epilactose, or zinc.

There have been no teachings, suggestions, and/or implications about the use of NSAID+Epi+Zn or its derivatives for the treatment of inflammation, fever or pain. This is the first evidence of data reported or documented on a formulation comprising pharmaceutically active combinations of NSAID, epilactose, and zinc. Given the increase in efficacy and decreased toxicity for NSAIDS disclosed herein, previous uses or applications reported as either appearing ineffective or with increased toxicity or undesired side effects must be revisited. Therefore, though many uses of NSAIDS are known to those in the art and disclosed herein no list can be considered all inclusive, and any use of the composition(s) disclosed herein are the object of this invention. The present inventors have discovered that the composition with a combination of NSAID, epilactose and a zinc salt, designated as 'NSAID+Epi+Zn' in this invention has synergistic effects and profound clinical benefit in the effective treatment of acute and chronic pain, fever, and inflammation when compared to several other combinations and commercially available conventional formulations of NSAIDs.

The present invention is readily carried out as described herein.

DEFINITIONS

As used herein, the singular forms "a", "an", and "the" include plural referents unless the context clearly dictates otherwise. Thus, for example, reference to "a compound" includes a plurality of such compounds.

The term "Pharmaceutically acceptable" as used herein means that which is useful in preparing a pharmaceutical composition that is generally safe, non-toxic and neither biologically nor otherwise undesirable and includes that which is acceptable for veterinary use as well as human pharmaceutical use.

As used herein, the term "effective amount" essentially means the same thing as the phrase "pharmaceutically effective amount" or the term "therapeutically effective amount" and refers to the amount of a compound or a combination of compounds of the compositions disclosed in this invention or other similar things used for experimental purposes herein and comparison of efficacies, that, when administered to a mammal for treating a state, disorder or condition, is sufficient to effect such treatment. The "therapeutically/pharmaceutically effective amount" will vary depending on the compound, the disease and its severity and the age, weight, physical condition and responsiveness of the mammal to be treated.

The term 'treat', "treating" or "treatment" of a state, disorder or condition as used herein means: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statistically significant or at least perceptible to the patient or to the physician.

For example, the term 'treatment of pain' as referred herein specifically means administration of therapeutically effective amount of a composition of this invention or an equivalent compound to a mammal for providing relief from pain (which is further defined as unpleasant sensory and emotional experience and other distressing symptoms) as a result of acute surgical conditions such as appendicitis, peritonitis etc. or road accidents or due to chronic ailments such as rheumatoid arthritis, osteoarthritis, spondylosis etc. Similarly, the term 'treatment of inflammation' as referred herein refers to administration of therapeutically effective amount of a composition of this invention or an equivalent compound to a mammal for providing relief from inflammation accompanying acute pain as well as long term persistent medical conditions, such as rheumatoid arthritis, osteoarthritis, spondylosis etc.

The term 'triple composition' or 'triple combination' as used herein refer to a composition containing three main components, one of which is a preferred NSAID, the other, epilactose and the third a suitable zinc salt all in pharmaceutical acceptable doses. Likewise, a 'double combination' refers to a composition containing two main components, one of which is a preferred NSAID and the other, epilactose.

The term, 'NSAID' or 'non-steroidal anti-inflammatory drugs' as used herein mean those medicines which have been duly approved by authorized agencies for marketing and clinical use in USA and/or other countries and are within the scope of sound medical judgment for treatment of various medical conditions and which belong to various sub-categories based on their chemical structures and/or functions and as described in detail in 'Background to the Invention' in this patent application.

The term 'mammal' as used herein is equivalent to the terms 'patient' and/or 'subject' in need of a treatment for a medical indication and could be living human or an animal such as cat, dog, cattle etc.

As used herein, "pharmaceutically acceptable salts" refer to derivatives of the pharmaceutical active compounds wherein the parent compound is modified by making add or base salts thereof. Generally, such salts can be prepared, as known to person skilled in the art, by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington Pharmaceutical Sciences, 19th ed. (Mack Publishing Company, 1995) and Remington: The Science and Practice of Pharmacy, 20th Edition, Baltimore, Md.; Lippincott Williams & Wilkins, 2000, which are incorporated by reference herein in their entirety.

Further, in the specification, the singular forms also include the plural, unless the context clearly dictates otherwise. Unless defined otherwise, all technical and scientific terms used herein have the same meaning as commonly understood by one of ordinary skill in the art to which this invention belongs, in the case of any conflict, the present specification will prevail. Also, all percentages and ratios used herein, unless otherwise indicated, are by weight.

Having decided about the key ingredients of new compositions, several preferred embodiments comprising of combinations of an NSAID and epilactose with or without a pharmaceutically acceptable zinc salt were prepared for experimental purposes and to test the mode of enablement of our invention. Preparatory methods of these embodiments are described below in the following examples.

The first of these pharmaceutical active moieties is NSAID as defined above. For preferred embodiments for practical validation of this invention, the NSAIDs used herein included ibuprofen, naproxene, and celecoxib, and/or pharmaceutically acceptable salt thereof. The average particle diameter or size of the active moiety of NSAID (e.g., ibuprofen) or a pharmaceutically acceptable salt thereof identified was not less than 1 nanometer and not more than 600 micrometers.

The formulation in this inversion also comprises of the chemical compound, epilactose, also known as 2-epi-lactose; 4-O-B-galactopyranosyl-D-mannopyranose or 4-o-β-galactopyranosyl-d-mannopyranose or 4-O-b-Galactopyranosyl-D-mannopyranoside or 4-O-SS-Galactopyranosyl-D-Mannopyranoside or 4-O-Beta-Galactopyranosyl-D-Mannopyranoside or 4-O-(b-D-Galactopyranosyl)-D-mannopyranoside. The average particle diameter or size of the epilactose used in these compositions was not less than 1 nanometer and not more than 600 micrometers.

The third key constituent in the formulations disclosed in this invention comprises of one or more pharmaceutically acceptable divalent zinc salt as defined above. For validation of this invention, the preferred embodiments included zinc chloride, zinc carnosine, and zinc stearate having the average particle diameter or size not less than 1 nanometer and not more than 600 micrometers.

In one embodiment, the NSAID (e.g., Ibuprofen) or a pharmaceutically acceptable salt thereof may be converted into the zinc complex of NSAID (e.g., Ibuprofen) either during the manufacturing process or as an intermediate processing step. In this embodiment, the active ingredient used in the formulation to produce the finished product will be a Zinc complex of NSAID (e.g., Ibuprofen) as per the following equation:

$$2R-COOH + Zn^{++} \rightarrow (R-COO)_2Zn + 2H^+$$

where, R—COOH is NSAID (e.g., Ibuprofen); $Zn^{++}$ represents the zinc salt in its ionic form (divalent state) described above; $(R-COO)_2Zn$ is the zinc salt of NSAID; and $H^+$ is hydrogen ion as released in the reaction. In this embodiment, as an example, if ibuprofen and zinc chloride are used to prepare the Zn complex, the chemical reaction would be as follows:

$$2C_{13}H_{18}O_2 + ZnCl_2 \rightarrow (C_{13}H_{17}O_2)_2Zn + 2HCl$$

The divalent zinc complex of ibuprofen, in this embodiment, is prepared by dispersing ibuprofen base in water (vehicle). The pH of the dispersion is maintained at 6 to 10 using sodium hydroxide or any other suitable alkali. Zinc chloride is also dissolved in water (vehicle). The ibuprofen preparation and the zinc chloride solutions are mixed together. The precipitate of zinc complex of ibuprofen is removed from the mixture by filtration and washed with water to remove trace amount of sodium and/or chloride ions.

In a preferred embodiment, the selected compounds are processed together so as to occur ionic reaction between the select NSAID and the divalent metal compound and/or bound chemically and/or held mechanically as admixture together and may be allowed to form a strong or weak complex within the matrix of the blended media. The preparation may be aimed at to form a uniform or non-uniform powder mix, multi-particulate powder blend, solution, suspension, dispersion, emulsion, ointment, or a cream prepared either geometrically or by simple mixing or trituration. These preparations could be with or without pharmaceutically acceptable functional ingredients including but not limited to the diluents, binders, lubricants, disintegrant, wetting agents, anionic or nonionic surfactants, solubilizing agents, solvents, vehicles, flavoring agents, glidants, gums, humectants, monovalent and/or divalent and/or trivalent and/or tetravalent metals and their salts, plasticizers, preservatives, suspending agents, sweeteners and viscosity modifiers collectively referred to herein as "carrier materials". These preparation may be prepared for the variety of end uses, such as oral (e.g., tablets, capsules, liquid preparations), intravenous (bolus or infusion), intraperitoneal, topical (e.g., ocular, eye drop, semi-solid preparations), subcutaneous, vaginal, rectal, intramuscular, transdermal (e.g., patch) and intranasal administrations. An effective but non-toxic amount of the these preparations as desired can also be employed as a treatment for dental lesions.

A large number of formulations as per above compositions were prepared and tested for their efficacies and other effects as compared to those tested elsewhere to demonstrate the synergistic therapeutic effect. Selected examples of final formulations experimented in this invention are shown in Table 1.

TABLE 1

Select examples of final formulations experimented in this invention are shown.

| Ingredient | % w/w |
|---|---|
| Example 1 | |
| Purified water | q.s. |
| Ibuprofen | 90 |
| Epilactose | 0.09 |
| Zinc Carnosine | 5 |
| Dibasic Calcium Phosphate | 1 |
| Croscarmellose sodium | 1 |
| Microcrystalline cellulose | 1.11 |
| Sodium Lauryl Sulphate | 1 |
| Ethyl cellulose | 0.5 |
| Colloidal Silicon Dioxide | 0.3 |
| Example 2 | |
| Purified water | q.s. |
| Ibuprofen | 40 |
| Epilactose | 45 |
| Zinc Chloride | 10.05 |
| Calcium Carbonate | 1 |
| Sodium starch glycolate | 1 |
| Lactose | 1.15 |
| Zinc Stearate | 1 |
| Povidone | 0.5 |
| Talc | 0.3 |
| Example 3 | |
| Purified water | q.s. |
| Ibuprofen | 40 |
| Epilactose | 0.05 |
| Zinc Carnosine | 55 |
| Dibasic Calcium Phosphate | 1 |
| Croscarmellose sodium | 1 |
| Microcrystalline cellulose | 1.15 |
| Sodium Lauryl Sulfate | 1 |
| Ethyl cellulose | 0.5 |
| Colloidal Silicon Dioxide | 0.3 |
| Example 4 | |
| Purified water | q.s. |
| Naproxen | 14 |
| Epilactose | 85 |
| Dibasic Calcium Phosphate | 0.1 |
| Croscarmellose sodium | 0.1 |
| Mannitol | 0.1 |
| Magnesium Stearate | 0.2 |
| Polymethacrylate | 0.2 |
| Colloidal Silicon Dioxide | 0.1 |
| Example 5 | |
| Purified water | q.s. |
| Celecoxib | 39 |
| Epilactose | 7 |
| Zinc Carnosine | 49 |
| Dibasic Calcium Phosphate | 1 |
| Croscarmellose sodium | 1 |
| Mannitol | 1.2 |
| Magnesium Stearate | 1 |
| Polymethacrylate | 0.5 |
| Colloidal Silicon Dioxide | 0.3 |
| Example 6 | |
| Purified water | q.s. |
| Naproxen | 88 |
| Epilactose | 7 |
| Zinc Chloride | 0.09 |
| Dibasic Calcium Phosphate | 1 |
| Croscarmellose sodium | 1 |
| Microcrystalline cellulose | 1.11 |
| Sodium Lauryl Sulphate | 1 |
| Ethyl cellulose | 0.5 |
| Colloidal Silicon Dioxide | 0.3 |
| Example 7 | |
| Purified water | q.s. |
| Ibuprofen | 9 |
| Epilactose | 0.2 |
| Zinc Chloride | 90 |
| Calcium Carbonate | 0.1 |
| Sodium starch glycolate | 0.1 |
| Lactose | 0.1 |
| Zinc Stearate | 0.2 |
| Povidone | 0.2 |
| Talc | 0.1 |
| Example 8 | |
| Purified water | q.s. |
| Ibuprofen | 58 |
| Epilactose | 37 |
| Dibasic Calcium Phosphate | 1 |
| Sodium starch glycolate | 1 |
| Microcrystalline cellulose | 1.2 |
| Zinc Stearate | 1 |
| Povidone | 0.5 |
| Colloidal Silicon Dioxide | 0.3 |

Several experimental conditions were tested with these compositions against single component doses of key NSAID used in the above formulations as well as other single component NSAIDs and plain epilactose and a relevant line salt. Thus, these included the following:

a) Epilactose (Epi)
b) Zinc Carnosine (ZnCar)
c) Ibuprofen (Ibu)
d) Naproxen (Nap)
e) Celecoxib (Cox)
f) Ibuprofen with Epilactose (Ibu+Epi)
g) Ibuprofen with Zinc Chloride (Ibu+ZnCl)
h) Ibuprofen with Zinc Stearate (Ibu+ZnSt)
i) Ibuprofen with Zinc Carnosine (Ibu+ZnCar)
j) Ibuprofen with Epilactose and Zinc Chloride (Ibu+Epi+ZnCl)
k) Ibuprofen with Epilactose and Zinc Carnosine (Ibu+Epi+ZnCar)

C57Bl/6 mice and Sprague-Dawley (SD) rats were used. Animals were group-housed under controlled temperature (25° C.) and photoperiods (12:12-hour light-dark cycle), and allowed unrestricted access to standard diet and tap water, unless otherwise noted. Animals were allowed to acclimate to these conditions for at least 7 days before inclusion in experiments. For each group of experiments, animals were matched by age, sex, and body weight. Care and experimentation of mice were performed in accordance with guidelines under protocols approved by the Institutional Animal Care and Use Committee.

To evaluate the effects of pain, the analgesic effects of Epi, ZnCar, Ibu, Nap, Cox, Ibu+Epi, Ibu+ZnCl, Ibu+ZnSt, Ibu+ZnCar, Ibu+Epi+ZnCl, and Ibu+Epi+ZnCar were tested in acetylcholine-induced (8.3 mg/kg, i.p.) mouse writing model. Seven mice were used in each group and were administered drugs orally at predetermined ED50 dose ranges. Thirty minutes after the oral administration of test drug, mice were provided with an intraperitoneal injection of 5.5 mg/kg acetylcholine bromide. Mice were then observed for the presence or absence of a characteristic behavioral response (a wave of constriction and elongation passing caudally along the abdominal wall, accompanied by a twisting of the trunk and followed by extension of the hindlimbs). The number of writhes was counted for 30 min and percentage nociception was calculated and correlatively compared between the groups. With the exception of Epi and ZnCar, all formulations demonstrated significant and marked clinical antinociceptive response, $p<0.05$ (FIG. 1). This suggested that epilactose and zinc carnosine did not exhibit therapeutic efficacy in the management of acute pain. Furthermore, Ibu+Epi+ZnCar demonstrated superior and significant clinical response to pain when compared to Ibu, Hap, and Cox, $p<0.05$ (FIG. 1).

To evaluate the effects of inflammation, Epi, ZnCar, Ibu, Nap, Cox, Ibu+Epi, Ibu+ZnCl, Ibu+ZnSt, Ibu+ZnCar, Ibu+Epi+ZnCl, and Ibu+Epi+ZnCar were administered in specific predetermined doses. Six rats were used in each group. Carrageenin-induced hind paw edema was established in SD rats using Lambda-carrageenin solution injected so into the right hind paw within the first hour of oral administration of these drugs. The paw volume was estimated using a plethysmometer both at baseline and three hours following induction. With the exception of Epi and ZnCar, all formulations demonstrated significant and marked clinical response 3 hours after carrageenin injection. This again suggested that epilactose and zinc carnosine did not exhibit therapeutic efficacy in the management of acute inflammation. Ibu+Epi+ZnCar again demonstrated superior and significant clinical response to pain when compared to Ibu, Nap, and Cox, $p<0.05$.

While NSAIDs have immense therapeutic benefit, they also cause numerous side-effects, in particular gastro intestinal and renal toxicity. The gastro intestinal toxicity of NSAIDs can be broadly characterized into dyspepsia and abdominal pain, mucosal lesions and serious gastro intestinal complications, such as perforated ulcers or bleeding requiring hospitalization. Renal side-effects include fluid retention and hypertension, and in severe cases NSAIDs may precipitate congestive heart failure and renal failure. Given that all NSAIDs, including low-dose aspirin, increase the risk of serious complications, the present inventors performed elaborate investigations with the above formulations to correlate adverse effect profiles when compared to conventional NSAIDs. This elicited both surprising and highly interesting novel results for gastroprotective and renoprotective synergistic effects when treated with Ibu+Epi+ZnCar.

To evaluate gastroprotective effects, ulcerogenicity was determined using standard protocols. Eight rats were used in each group. Ulcerogenic activity was evaluated after oral administration of Epi, ZnCar, Ibu, Nap, Cox, Ibu+Epi, Ibu+ZnCl, Ibu+ZnSt, Ibu+ZnCar, Ibu+Epi+ZnCl, and Ibu+Epi+ZnCar for 5 days. Animals were then sacrificed and the stomach was extracted, dissected along the greater curvature, washed and cleaned with distilled wafer and normal saline, and fixed by intraluminal irrigation with 2% formalin. The mucosal damage was examined by means of a stereoscopic microscope. Mucosal damage was assessed as follows: a. 0.5 for redness and erythema, b. 1 for spot ulcers, c. 1.5 for hemorrhagic streaks, d. 2 for ulcers < or equal to 5 and, e. 3 for ulcers >5. Severity index of gastric mucosal damage was calculated as the difference between the scores for each treated group from that of the control group.

Figure 2:
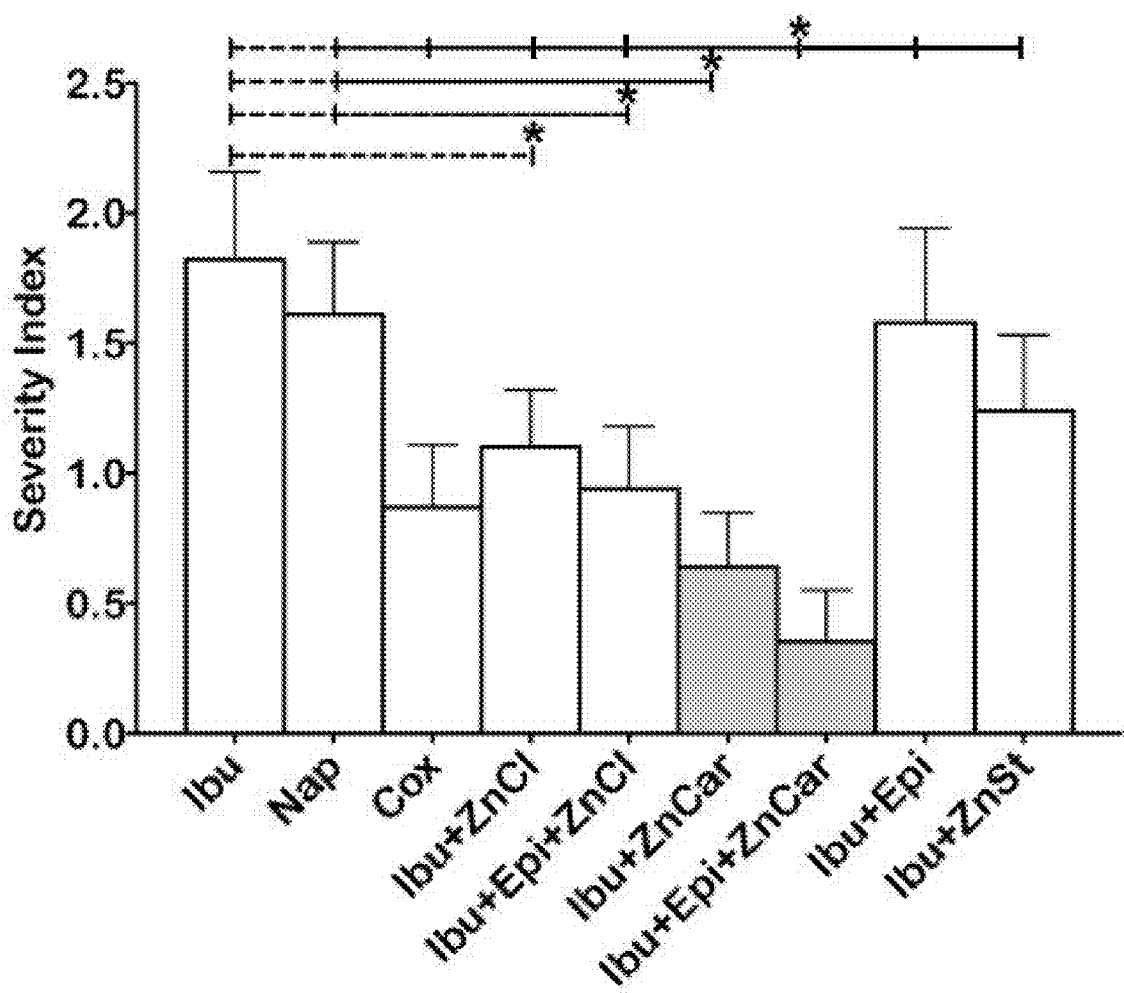
FIG. 2 is a histogram illustrating the gastroprotective safety profile of NSAID+Epi+Zn

As shown in FIG. 2, the studies depicted here show that addition of zinc had demonstrable gastroprotective effects when compared to NSAIDs. This is demonstrated by Ibu+ZnCl, Ibu+ZnSt, and Ibu–ZnCar. These effects were characterized as ZnCar>ZnCl>ZnSt. It is important to note that while Ibu+Epi did not exhibit significant changes, addition of Epi to Ibu when combined with zinc demonstrated significant changes. This is the most important aspect of the novelty of this work, which is best represented by Ibu+Epi+ZnCar. As shown in FIG. 2, Ibu+Epi+ZnCar demonstrated profound decreased severity scores when compared to Ibu, Nap, and even Cox, demonstrably indicating the powerful gastroprotective effects of Ibu+Epi+ZnCar in the therapeutic management of disease.

NSAID's are associated with clinically significant decreases in haemoglobin dependent and independent of acute bleeding events. Independent clinical trials of chronic NSAID use, two of them large studies composing respectively of 8059 and 4484 arthritic patients that were treated with chronic NSAIDs demonstrated that significant decreases in haemoglobin of $\geq 2$ g/dL occurred as a result of NSAID use. Low hemoglobin results in anemia, which is associated with adverse outcomes including disability, severe fatigue, morbidity, hypertension, dyspnea, and in serious cases secondary organ dysfunction and damage, including head arrhythmia and heart failure. This highlights the importance of developing safe NSAID drugs that can counter the clinical issue of long-term chronic occult blood loss.

Figure 3:
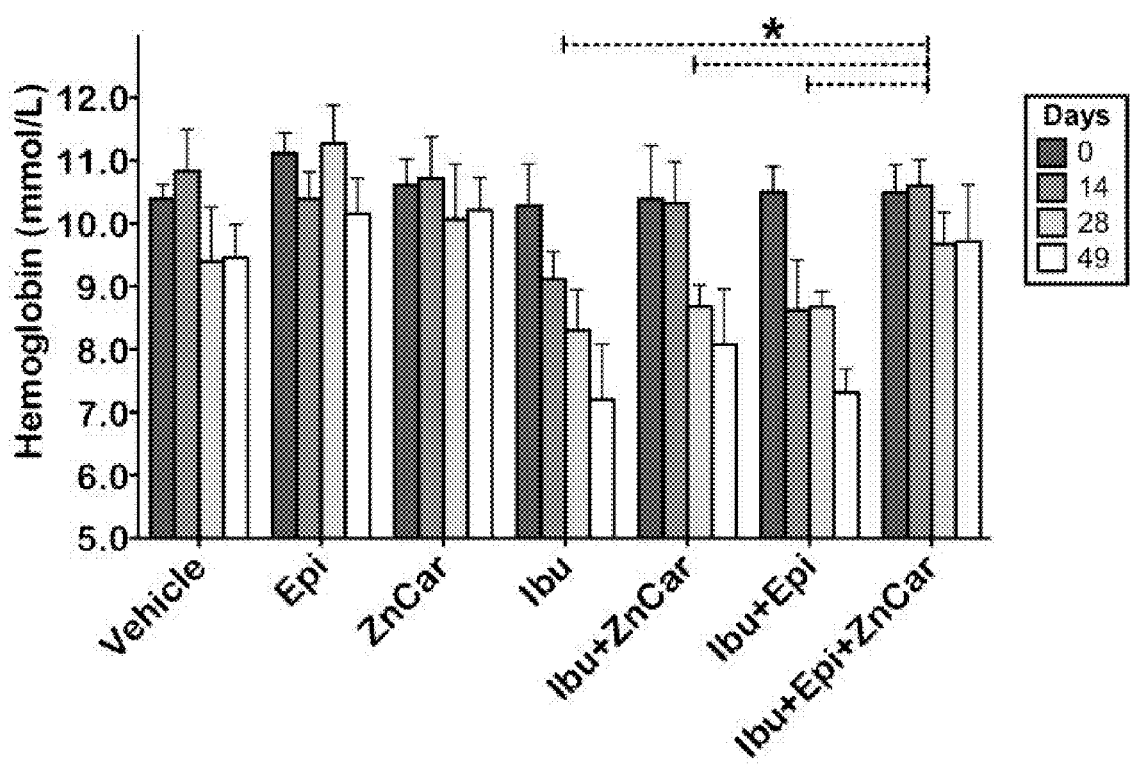
FIG. 3 is a histogram demonstrating the safety profile of NSAID+Epi+Zn with regard to hemoglobin loss.

To investigate changes in Hb, mice treated with Epi, Ibu, ZnCar, Nap, Cox, Ibu+Epi, Ibu+ZnCar, and Ibu+Epi+ZnCar were used. A total of 5 mice per group were used. Mice were followed for seven weeks and blood was drawn on days 0, 14, 28, and 49. Hemoglobin was assessed in blood drawn from mice using a HemoCue Hb 201 analyzer. A drop of mouse blood was placed on a HemoCue microcuvette and assessed immediately. Measurements were recorded in millimole per liter. As shown in FIG. 3, mice treated with Ibu demonstrated a progressive highly significant decrease in hemoglobin, demonstrably due to the effects of NSAID. Mice treated with Nap and Cox also demonstrated a progressive decrease in hemoglobin (data not shown). Strikingly, mice treated with Ibu+Epi+ZnCar had significant (p<0.05) and clinically relevant protection from loss of hemoglobin. (FIG. 3). The results were also interesting given that neither the Ibu+Epi treatment nor Ibu+ZnCar treatment arms were effective enough to prevent Hb loss. This suggests the likelihood of a synergistic therapeutic effect of Ibu+Epi+ZnCar when compared to Ibu+Epi, Ibu+ZnCar, and/or Ibu alone.

NSAIDs are also notorious for their renal side-effects which include fluid retention and hypertension, precipitating congestive heart failure and renal failure. The above mentioned anemia related effects of NSAIDs can also contribute to progression of kidney disease, since anemia is a potent modulator of renal hemodynamics. Anemia decreases the efficiency of systemic oxygen delivery, thereby resulting in increased heart rate, cardiac output, and hypertension. Renal ischemia can be caused by reduced oxygen delivery due to low Hb and underlying heart failure. The kidney compensates by producing hormones (hypersecretion of renin, which accelerates conversion of angiotensin I to angiotensin II) that exerts a vasoconstrictive effect and increase blood pressure resulting in renovascular hypertension. Left untreated, this can lead to heart attack, stroke or kidney failure.

The present inventors evaluated for the effects of renovascular hypertension by assessing blood pressure, renin, and serum creatinine following treatment with Epi, Ibu, ZnCar, Nap, Cox, Ibu+Epi, Ibu+ZnCar, and Ibu+Epi+ZnCar. Renin and creatinine results suggest striking synergistic effects of Ibu+Epi+ZnCar. Heart rate and systolic BP were measured daily by a non-invasive method. This utilized tail-cuff plethysmography using a model BP-2000 Visitech Blood Pressure System. Mice were trained for an initial period, followed by subsequent measurement collection. While mice treated with Ibu, Nap, and Cox demonstrated significant elevations in systolic blood pressure (mean for Ibu 129.3 mmHg+/−6.7), mice treated with Ibu+Epi+ZnCar exhibited levels demonstrably and significantly equivalent to controls (mean for Ibu+Epi+ZnCar 113.1 mmHg+/−5.2). Levels were statistically significant at p<0.05. Furthermore, changes in the levels of Ibu+Epi and/or Ibu+ZnCar were not statistically significant relative to Ibu alone. These results also suggest the synergistic potential of safety profiles of Ibu+Epi+ZnCar when compared to Ibu+Epi, Ibu+ZnCar, and/or Ibu alone.

Synergy was calculated using the industry accepted method described by Kull et al. (Kull F. C., Eisman, P. C., Sylwestrowicz, H. D. and Mayer, R. L., *Applied Microbiology* 9:538-541, 1961). This is mathematically demonstrated as:

$$(Qa/QA)+(Qb/QB)+(Qc/QC)=\text{Synergy Index }(SI)$$

where, QA=concentration of NSAID alone needed to achieve a specified end point, Qa=concentration of NSAID in the combination NSAID+Epi+Zn needed to achieve a specified end point, QB=concentration of Epi alone needed to achieve a specified end point, Qb=concentration of Epi in the combination NSAID+Epi+Zn needed to achieve a specified end point, QC=concentration of ZnCar alone needed to achieve a specified end point, Qc=concentration of ZnCar in the combination NSAID+Epi+Zn needed to achieve a specified end point. A SI value of 1.0 indicates additivity, an SI value greater than 1.0 is indicative of antagonism, and a SI value of less than 1.0 is indicative of synergy. With the endpoint in the analysis set for a combined gastroprotective and renoprotective safety index score, the calculated synergy index for NSAID+Epi+Zn is 0.51. Since the synergy index for the combination NSAID+Epi+Zn is less than 1.0, the combination is synergistic.

When this analysis was reevaluated with double combinations NSAID+ZnCar, or ZnCar+Epi, the synergy index was greater than 1.0, suggesting a lack of synergy. The third double combination NSAID+Epi obtained a synergy index of 0.96, which was closer to additivity than synergism and significantly lower than that of the combination NSAID+Epi+Zn. Therefore, the presence of all three components NSAID, Epi, and ZnCar was necessary to achieve the observed synergistic safety and efficacy of the NSAID+Epi+Zn combination as a whole.

Finally, these preclinical studies also demonstrated the ability to use low concentrations of NSAIDs, Epi and Zn in our combinations of NSAID+Epi+Zn to obtain higher levels of safety with effective analgesic efficacy, and therefore synergy. Our compositions therefore are composed of NSAIDs that, in our combination of NSAID+Epi+Zn, can be used at concentrations lower than required individually to achieve analgesic efficacy.

Figure 4:
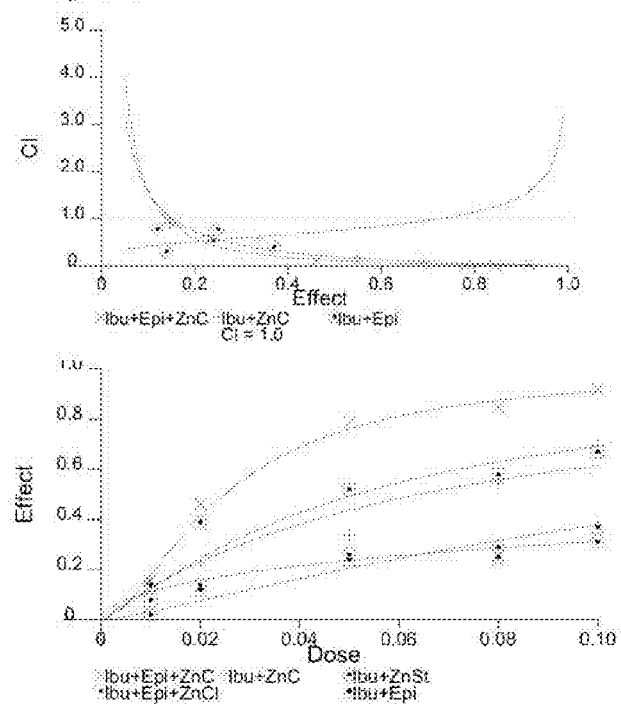
FIG. 4 is a set of graphs showing the results of an isobolographic analyses on synergistic effects of NSAID+Epi+Zn when compared to the other NSAID formulations studied in this application based on the combined gastroprotective and renoprotective safety scores.
Figure 4:
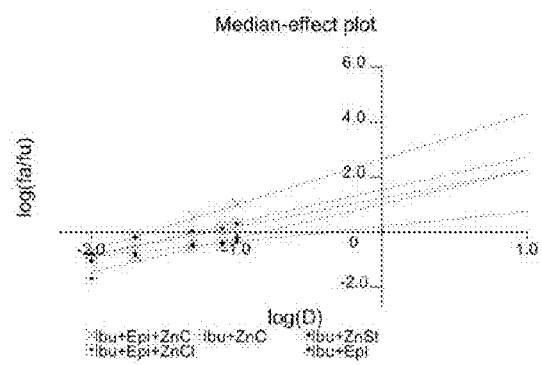
Figure 5:
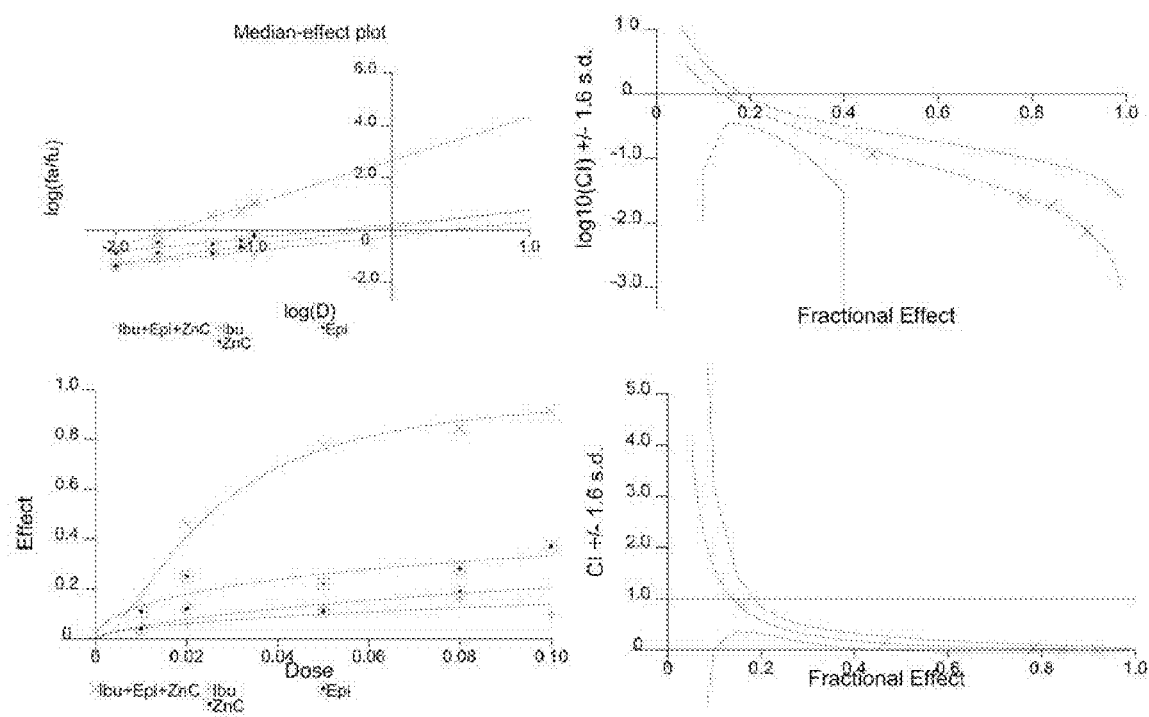
FIG. 5 is a continuation of set of graphs showing the combined gastroprotective and renoprotective safety index and synergistic effect of triple combination of NSAID+Epi+Zn.

To further evaluate the role of synergistic interactions between the different combinations, an isobolographic analysis was conducted on the safety index from the gastrointestinal, hemoglobin and renal studies conducted herein on all NSAID formulations. As shown in FIGS. 4 and 5, Ibu+Epi+ZnCar demonstrated a strong synergistic interaction when compared to Ibu+Epi or Ibu+ZnCar. Furthermore, as shown in the dose effect (FIGS. 4 and 5) from the analysis, Ibu+Epi+ZnCar performed at statistically significant superior levels when compared to Ibu, Epi, Ibu+ZnCl, and/or Ibu+ZnStearate.

Thus, as exemplified above, the present inventors have identified, developed and tested novel compositions containing a triple combination of a NSAID, epilactose, and zinc. In so doing, the inventors ware able to successfully demonstrate these compositions to have novel synergistic effects and significant safety profiles when compared to individual or double combinations of NSAID, Epilactose, or Zinc alone.

When claimed, zinc, epilactose, non-steroidal drugs or NSAIDs, acetaminophen, and other compounds should be to mean any of its pharmaceutically acceptable salt or solvate Zinc may also refer to any one of it's salts such as sulfate, acetate, borate, bromide, benzoate, carbonate, chloride, citrate, diacetate gluconate, glycinate glycerophosphate, hexafluorosilicate, nitrate, oxide, peroxide, phosphate, phenol, sulfonate, salicylate, silicate, stannate, tannate, tetrafluoroborate, titanate, and trihydrate or could be from any other pharmaceutically acceptable source of zinc as known in the art. Any molecular manipulation that would be considered a salt of zinc, is included and claimed herein.

When claimed non-steroidal drugs or NSAIDs may be any one of antipyrine, aminopyrine, aminopyrone, aleofenac, apazone, benzydamine, bucolome, celecoxib, cinchophen, choline magnesium trisalicylate, clofezone, clonixin, diclofenac, diflunisal, dipyrone, ditrazol, epirizole, etodolac, etoricoxib, ibuprofen, indomethacin, indoprofen, fenoprofen, floctafenin, flufenamic acid, flurbiprofen, glaphenine, ketoprofen, ketorolac, loxoprofen, meclofenamic acid, mefenamic acid, meloxicam, nabumetone, naproxen, niflumic acid, oxaprozin, oxyphenbutazone, parecoxib, phenacetin, phenylbutazone, prenazone, piroxicam, tebufelone, tenidap, rofecoxib, salicylic acids, salidifamides, sulindac, suprofen, tolmetin, valdecoxib, and any other drug duly approved for treatment of indications requiring administration of NSAID, as well as compounds not approved that would be considered a non-steroidal drug by those of ordinary skill in the art.

Administered, administration of, or route of administration refers to delivery of the compound to a subject through intraperitoneal, oral gavage, intravenous, sublingual, topical, intramuscular, intra-arterial, intramedullar, intrathecal, intraventricular, transdermal, subcutaneous, intranasal, parenteral, rectal or through any other alternative route of drug administration demanded by clinical situation or that would be known to those skilled in the art.

Subject herein may refer to a patient, a human, a primate, or a mammal.

Condition when claimed may refer to pain, fever, or inflammation, among others, including ankylosing spondylitis, aplastic anemia, asthma, Behcet's syndrome, burns including injuries due to radiation and corrosive chemicals, bursitis, bone fracture and/or dislocation of joints, bronchitis, cardiopulmonary syndrome, cellular neoplastic transformations or metastic tumor growth, common cold and other viral infections, conjunctivas, damage of one or more connective tissues, degenerative joints, fever (pyrexia), functional dyspepsia, gastrointestinal conditions, gingivitis, glomerulonephritis, gout, headache, Hodgkin's disease, hypersensitivity, immune and autoimmune diseases, inflammations that occur as sequellae to influenza, inflammatory disorders of the skin, inflammatory bowel disease including Crohn's disease and ulcerative colitis, irritable bowel syndrome, juvenile rheumatoid arthritis, menstrual cramps and/or pain, migraine and pain associated with migraine, myasthenia gravis, myocardial ischemia, neck pain, back pain, nephrotic syndrome, osteoarthritis, periarteritis nodosa, polymyositis, post partum pain, psoriasis, psoriatic arthritis, neuralgia, rheumatic fever, rheumatoid arthritis, sarcoidosis, sclerodema, Sjogren's syndrome, sprains, skeletal pain, strains, synovitis, systemic lupus erythematosus, sunburns, tendinitis, toothache and/or pain due to surgical and dental procedures, thyroiditis, vascular diseases, vasculitis or any other indication associated with pain and inflammation of known or unknown origin, and others.

Medication form refers to such medical items as a tablet, hard or soft gelatinous capsule filled with solid, liquid or semi-solid content, solution, liquid, elixir, syrup, cough drop, jelly, lozenges, lollipop, gum, aqueous or oily suspension, dissolvable strip, dispersible powder or granules, drug layered sugar shares or substrates for oral use, ii) cream, ointment, gel, foam, paste, powder, throat spray, nasal spray, liquid spray, mouth wash, gargle, inhalable particles, inhalable solutions, droplets, aerosol, emulsion, lotion, impregnated dressings, transdermal patch for topical use, iii) injectible for subcutaneous (sc) injection, pre-filled syringe or in any other medication form or medicated devices demanded by clinical situation such as microcapsules, suppository, ocular etc. which may additionally contain carriers or vehicles, fillers, disintegrators, lubricants, glidants, binders, disintegrators or disaggregators and coatings as known in the art aimed at pulsatile, sustained, delayed or controlled-release, immediate or modified-release mode of action as known in the art.

The compositions can be optimized in designing the drug formulation of different concentrations of each component and the dosage units thus obtained are combinatorially optimized for the therapeutic synergy through its pharmacokinetic profile.

In some embodiments, the dosage or an 'effective amount' of the constituent NSAID selected ranges from 5 mg or more up to 3200 mg or more a day. The composition of claim 1 or 2 together with claims 6 and 7, wherein the dosage or an 'effective amount' of the constituent epilactose ranges from 0.1 mg to 500 mg or more per day. The composition of claim 1 or 2 together with claims 3, 4, 6 and 7, wherein the dosage or an 'effective amount' of the constituent zinc carnosine or any other zinc compound/salt ranges from 0.1 mg to 500 mg or more per day.

Formulations may be devised in certain embodiments to deliver active ingredient of NSAID or other constituents, viz., epilactose and zinc salt or a combination thereof in the plasma or other bodily fluids (including whole blood, serum, urine, saliva, CSF, or secretions) at a delivery rate of 0.1 to 900 or more µg/mL/min by way of administration of the drug as herein.

Medication form refers to those generally known in the art. When used the term carrier refers to drug carriers which may be selected from the following class of compounds and/or salts thereof: calcium silicate, carbomers, carboxy methyl cellulose, sodium, carrageenan, chitosan, colloidal silicon dioxide, gelatin, glyceryl palmitostearate, guar gum, hydroxy ethyl cellulose, hydroxy propyl cellulose, hydroxy ethyl methyl cellulose, microcrystalline cellulose and carboxymethyl cellulose sodium, polyethylene oxide, polyethylene glycol, polyethylene alkyl ethers, polymethacrylates, propylene carbonate, sodium ascorbate, sorbitol, sodium alginate, alginic acid, urethane, acacia, bentonite, cetostearyl alcohol, cyclomethicon, ethyl cellulose, glycerin, glyceryl behenate, hydrogenated vegetable oil type i, hypromellose, magnesium aluminum silicate, maltitol, maltodextrin, methyl cellulose, polydextrose, polyvinyl acetate phthalate, polyvinyl alcohol, potassium chloride, povidone, propylene glycol alginate, tragacanth, xanthan gum, starch of natural and/or synthetic origin, natural/synthetic cellulose derivatives of organic and/or inorganic acids and salts, monovalent/divalent/trivalent/tetravalent metallic salts of glycerols/organic acids/carboxylic acids including but not limited to stearic acid/palmatic acid/myrstic acid, talc, hydrogenated oils of natural and synthetic origin, natural and/or synthetic gums.

Drug delivery herein is defined as administering a compound in order to achieve a desired therapeutic effect. When referred to rate of drug delivery indicates the time elapsed after administration of a compound for the desired therapeutic effect to take place in the subject.

We claim:

1. A composition comprising i) ibuprofen or celecoxib or naproxen in an amount of about 0.5 mg to about 6400 mg; ii) epilactose in an amount of about 0.01 mg to about 1000 mg; and iii) zinc in an amount of about 0.01 mg to 1000 mg, wherein the composition has a Synergy Index less than 1.0.

2. The composition of the claim 1 wherein zinc consists essentially of zinc carnosine.

3. The composition of claim 1, wherein a condition in a mammal, a human, a livestock animal, or a companion animal is treated with the composition.

4. The composition of claim 1, wherein the composition is administered to a subject.

5. The composition of claim 1, wherein i) ibuprofen or celecoxib or naproxen and ii) epilactose are provided in separate dosage units as a liquid, solid, semi solid or combinations thereof.

6. The composition of claim 1 wherein the composition is formulated to deliver any of i) ibuprofen or celecoxib or naproxen; ii) epilactose; or iii) zinc to a subject's plasma, whole blood, serum, urine, saliva, cerebral spinal fluid or secretions at a rate to achieve a sustained release of the composition.

7. The composition of claim 1 wherein the composition is formulated to release 1 to 99 percent of the total unit dose of i) ibuprofen or celecoxib or naproxen; ii) epilactose; or iii) zinc or combinations thereof in an in-vitro system, with or without the use of a medium having a pH ranging from 1 to 8.5.

8. The composition of claim 1 prepared in the form of a tablet, capsule, granule, sphere, or multi-particulate preparation, and wherein the i) ibuprofen or celecoxib or naproxen; ii) epilactose; or iii) zinc are located in any of the core, matrix, or coating layer of hard shell capsules, soft gel capsules, or microcapsules.

9. The composition of claim 1 wherein the composition is formulated in a medication form which contains one or more carrier.

10. The composition of claim 9, wherein the carrier comprises one or more of calcium silicate, carbomers, carboxy methyl cellulose, carrageenan, chitosan, colloidal silicone dioxide, gelatin, glyceryl palmitostearate, guar gum, hydroxy ethyl cellulose, hydroxy propyl cellulose, hydroxy ethyl methyl cellulose, microcrystalline cellulose, sodium carboxymethyl cellulose, polyethylene oxide, polyethylene glycol, polyethylene alkyl ethers, polymethacrylates, propylene carbonate, sodium ascorbate, sorbitol, sodium alginate, alginic acid, urethane, acacia, bentonite, cetostearyl alcohol, cyclomethicon, ethyl cellulose, glycerin, glyceryl behenate, hydrogenated vegetable oil type I, hypromellose, magnesium aluminum silicate, maltitol, maltodextrin, methyl cellulose, polydextrose, polyvinyl acetate phthalate, polyvinyl alcohol, propyl alcohol, butyl alcohol, potassium chloride, povidone, propylene glycol alginate, tragacanth, xanthan gum, starch of natural and/or synthetic origin, natural or synthetic cellulose derivatives of organic or inorganic acids and salts, monovalent/divalent/trivalent/tetravalent metallic salts of glycerols/organic acids/carboxylic acids, talc, hydrogenated oils of natural and synthetic origin, or natural and/or synthetic gums.

11. The composition of claim 9 wherein the carrier is a solid, semisolid, solution, emulsion, dispersion, micelle, liposome, suspension, powder or combinations thereof.

12. The composition of claim 9 wherein the carrier comprises drug reservoirs, transporters, solubility enhancers, drug release modifiers, absorption enhancers, bioavailability modifiers, ADME modifiers, lubricants, disintegrants, diluents, binders, plasticizers, surfactants, fillers, colorants, or pH modifiers.

13. The composition of claim 9 wherein said carrier effects the rate of drug delivery by forming drug matrix reservoirs, undergoing ionic reactions, or forming molecular complexes.

14. The composition of claim 1 wherein the composition is formulated to deliver any of i) ibuprofen or celecoxib or naproxen, ii) epilactose; or iii) zinc to a subject's plasma, whole blood, serum, urine, saliva, cerebral spinal fluid or secretions at a rate to achieve a rapid release of the composition.

* * * * *